United States Patent [19]

Rieber et al.

[11] Patent Number: 4,673,429

[45] Date of Patent: Jun. 16, 1987

[54] NITRIFICATION-INHIBITING 1-HYDROXYPYRAZOLE DERIVATIVES

[75] Inventors: Norbert Rieber, Mannheim; Heinrich Boehm, Neuhofen; Ernst-Heinrich Pommer, Limburgerhof; Juergen Dressel, Neuhofen, all of Fed. Rep. of Germany

[73] Assignee: BASF Aktiengesellschaft, Ludwigshafen, Fed. Rep. of Germany

[21] Appl. No.: 711,204

[22] Filed: Mar. 13, 1985

[30] Foreign Application Priority Data

Mar. 14, 1984 [DE] Fed. Rep. of Germany .... 3409317.6

[51] Int. Cl.$^4$ .................. C05C 1/00; C07D 231/16
[52] U.S. Cl. .......................... 71/27; 71/902; 548/375; 548/376
[58] Field of Search .............. 548/375, 376; 71/1, 71/64.01, 902

[56] References Cited

U.S. PATENT DOCUMENTS

| | | | |
|---|---|---|---|
| 3,137,563 | 6/1964 | Newcomer et al. | 71/107 |
| 3,282,991 | 11/1966 | Klein et al. | 562/493 |
| 3,494,757 | 2/1970 | Osborne | 71/1 |
| 3,635,690 | 1/1972 | Griffith | 71/1 |
| 4,511,723 | 4/1985 | Rieber et al. | 548/376 |

FOREIGN PATENT DOCUMENTS

| | | | |
|---|---|---|---|
| 3205456 | 8/1983 | Fed. Rep. of Germany | 548/375 |
| 1592516 | 11/1977 | United Kingdom | 71/1 |

OTHER PUBLICATIONS

Chemical Abstracts, 158074r, vol. 91, 1979, p. 673.

*Primary Examiner*—John M. Ford
*Assistant Examiner*—Kurt G. Briscoe
*Attorney, Agent, or Firm*—Keil & Weinkauf

[57] ABSTRACT

1-Hydroxypyrazole derivatives of the formula (I)

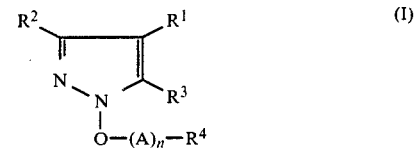

where A is

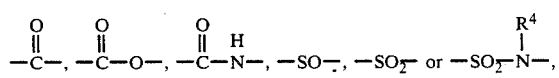

n is 0 or 1, $R^1$, $R^2$ and $R^3$ independently of one another are each hydrogen, chlorine, bromine or iodine, $R^4$ is hydrogen, a straight-chain or branched, open-chain alkyl, alkenyl or alkynyl radical, a cyclic alkyl, alkenyl or alkynyl radical or aryl or aralkyl, and the radicals $R^4$ which are capable of substitution may furthermore be monosubstituted or polysubstituted by halogen, haloalkyl, haloalkoxy, alkyl, alkoxy, alkoxycarbonyl, —OH, =O, —COOH or salts of this, —NO$_2$ or —CN, have a nitrification-inhibiting action. Substances where $R^4$ is not hydrogen when n is 0 are novel.

2 Claims, No Drawings

NITRIFICATION-INHIBITING 1-HYDROXYPYRAZOLE DERIVATIVES

The present invention relates to 1-hydroxypyrazoles and their reaction products, processes for their preparation, and compositions which contain these and are used for inhibiting nitrification of ammonium nitrogen.

Bound nitrogen for plant nutrition can be present in the soil in the form of ammonium compounds or of nitrates.

Bacteria of the genera Nitrosomonas and Nitrobacter oxidize ammonium nitrogen to nitrate nitrogen via nitrite nitrogen. The extent of nitrification is dependent on the type of soil and its pH, moisture content and biological activity. Nitrogen which is bound in the form of nitrate is more readily washed out than that bound in ammonium ions and is hence no longer available for plant nutrition; furthermore, undesirable concentration of nitrate in the groundwater is promoted by this process. Hence, the inhibition of nitrification is particularly important, and is generally considered to consist in selective ihibition of the growth of the abovementioned bacteria strains.

The use of N-substituted pyrazoles for the inhibition of nitrification has been disclosed (U.S. Pat. Nos. 3,494,757 and 3,635,690, German Laid-Open Application DOS 2,745,833 and British Pat. No. 1,592,516).

Moreover, 2-chloro-6-trichloromethylpyridine (nitrapyrin) and 3,5-dimethyltetrahydro-1,3,5-thiadiazine-2-thione (dazomet) are recommended for the inhibition of nitrification.

However, the conventional active ingredients do not meet all requirements in respect of efficiency, duration of action, cost-efficiency, lack of harmful effects, and performance characteristics such as water-solubility, dispersibility, vapor pressure, etc. Substances such as dazomet also have a very non-specific action and even attack soil bacteria which it is not intended to damage.

It is an object of the present invention to provide nitrification inhibitors which, if they have the above disadvantages at all, exhibit them to a lesser extent than the conventional agents of this type.

We have found that this object is achieved by 1-hydroxypyrazole derivatives of the formula (I)

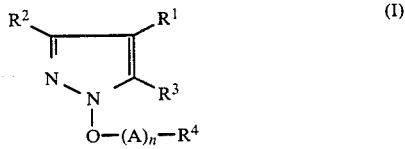

where A is

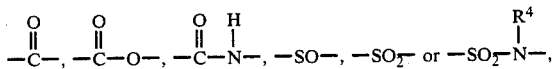

n is 0 or 1, $R^1$, $R^2$ and $R^3$ independently of one another are each hydrogen, chlorine, bromine or iodine, and $R^4$ is hydrogen or a straight-chain or branched, open-chain alkyl, alkenyl or alkynyl radical, a cyclic alkyl, alkenyl or alkynyl radical or aryl or aralkyl, and the radicals $R^4$ which are capable of being substituted may furthermore be monosubstituted or polysubstituted by halogen, haloalkyl, haloalkoxy, alkyl, alkoxy, alkoxycarbonyl, —OH, =O, —COOH or salts of this, —NO$_2$ or —CN.

Substances of the formula I in which $R^4$ is not hydrogen when n is 0 are novel substances. They can be obtained from the corresponding 1-hydroxypyrazoles, some of which likewise possess nitrification-inhibiting properties. These can be obtained by, for example, the methods described in German Laid-Open Applications DOS Nos. 3,031,385 and 3,205,456 and European Pat. No. 87,615. For example, the following 1-hydroxypyrazoles (n — 0, $R^4$ = H) are described there:

| Example | $R^1$ | $R^2$ | $R^3$ | Preparation according to |
|---|---|---|---|---|
| 162 | H | H | H | DOS 3,031,385, Example 1 |
| 163 | Cl | H | H | DOS 3,205,456, Table |
| 164 | Br | H | H | DOS 3,205,456, Example 1 |
| 165 | I | H | H | DOS 3,205,456, Example 3 |
| 166 | Br | Br | H | DOS 3,205,456, Table |
| 167 | Br | Br | Br | DOS 3,205,456, Table |
| 168 | Cl | Cl | Cl | DOS 3,205,456, Table |
| 169 | I | I | I | DOS 3,205,456, Example 2 |
| 170 | Cl | Br | Br | DOS 3,205,456, Example 4 |
| 171 | Cl | I | I | DOS 3,205,456, Table |

Aliphatic and aromatic 1-pyrazolyl compounds can be prepared in a conventional manner by reacting a 1-hydroxypyrazole with an aliphatic or aromatic halogen compound, hydrogen halide being eliminated. To do this, the reactants are heated, preferably in a solvent and in the presence of a base, eg. a tertiary amine, an alkali metal carbonate or sodium methylate or hydride. Often, the reaction begins at as low as room temperature, but occasionally only at as high as 180° C. The 1-pyrazolyl carboxylates, 1-pyrazolyl carbonates and 1-pyrazolyl sulfonates of the formula I can be prepared by a conventional method, by reacting a 1-hydroxypyrazole with acyl halide, a sulfonyl halide or a chlorocarbonate. In the presence of a base, this reaction frequently takes place at from as low as $-30°$ C. to $80°$ C.

1-Pyrazolyl carbamates of the formula I are obtained by a conventional method, by reacting a 1-hydroxypyrazole with an aliphatic or aromatic isocyanate simply by mixing the components, in general at above 0° C., in a solvent.

Iodopropargyl ethers of 1-hydroxypyrazoles are obtained, for example, from the corresponding propargyl ethers of the 1-hydroxypyrazoles by reaction with iodine at from 20° to 80° C., with elimination of hydrogen iodide. The presence of a base is advantageous.

1-Pyrazolyloxycarboxylic acids can be prepared by hydrolysis of alkyl 1-pyrazolyloxycarboxylates (mixed pyrazolyl-alkyl-carbonic acid esters) by a conventional method; in the case of alkaline hydrolysis with aqueous sodium hydroxide solution, the reaction takes place in general at below 80° C., only the alkyl radical being hydrolyzed.

The novel substances shown in the Tables below were prepared as described in the detailed Examples above the particular table, and, where one or more physical properties are stated, their structure was confirmed by conventional methods. The compounds listed without physical data can readily be obtained by appropriately modifying the stated methods of preparation.

EXAMPLE 1

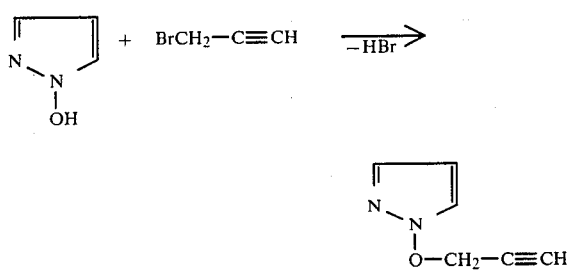

21.3 g of propargyl bromide are added to 15 g of 1-hydroxypyrazole and 15 g of sodium carbonate in 200 g of acetonitrile at 25° C., while stirring. Stirring is continued for 12 hours, after which the mixture is filtered under suction, the residue is washed with 100 g of acetonitrile, and the combined liquids are evaporated down in a rotary evaporator at 40° C. and under 20 mbar. The residue obtained in this procedure is dissolved in 200 g of dichloromethane, the solution is extracted 3 times with a total of 200 g of saturated aqueous sodium bicarbonate solution, and the organic phase is dried with magnesium sulfate and evaporated down. 15 g (70% of theory) of 1-pyrazolyl propargyl ether are obtained as an oil (H$^1$-NMR, δ in ppm: 2.6, t, 1H; 4.9, d, 2H; 6.2, m, 1H; 7.4, m, 2H). This substance is Example 10 in the Table below.

EXAMPLE 2

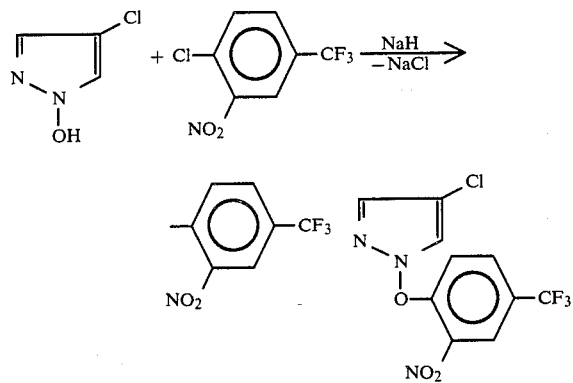

20 g of 4-chlorohydroxypyrazole, 6 g of NaH and 30 g of 1-chloro-2-nitro-4-trifluoromethylbenzene are stirred for 25 hours at 80° C., after which the mixture is cooled to 25° C., undissolved material is filtered off, the residue is washed with 100 g of acetonitrile, and the solution is evaporated down in a rotary evaporator at 40° C. and under 25 mbar. The residue is dissolved in 250 g of dichloromethane, the solution is extracted 3 times with a total of 200 g of 1% strength aqueous sodium hydroxide solution and then 3 times with a total of 200 g of water, and the organic phase is dried with magnesium sulfate and then evaporated down. 25 g (60% of theory) of 1-(2-nitro-4-trifluoromethylphenoxy)-4-chloropyrazole are obtained as an oil (H$^1$-NMR, δ in ppm: 6.8, d, 1H; 7.3, s, 1H; 7.6, s, 1H; 7.7, d, 1H; 8.2, bs, 1H). This substance is Example 49 in the Table below.

In the Table below, the boiling point if based on atmospheric pressure if no index is given; where an index is stated, this is in mbar.

TABLE 1 structure with $R^1$, $R^2$, $R^3$ on pyrazole ring, $O-(A)_n-R^4$ on N, $n = 0$

| Example | R$^1$ | R$^2$ | R$^3$ | R$^4$ | Mp. [°C.] |
|---|---|---|---|---|---|
| 3 | H | H | H | CH$_3$ | bp. 132 |
| 4 | Cl | " | " | " | Oil |
| 5 | H | " | " | cyclopropyl | bp.$_{20}$86 |
| 6 | " | " | " | (CH$_3$)$_2$CH— | bp.$_{18}$75 |
| 7 | " | " | " | (CH$_3$)$_3$C— | bp.$_{20}$90 |
| 8 | " | " | " | CH$_2$=CH—CH$_2$— | bp. 168 |
| 9 | " | " | " | Cl$_2$C=CCl—CH$_2$— | " |
| 10 | Cl | " | " | NC—CH$_2$— | Oil |
| 11 | I | " | " | HC≡C—CH$_2$— | Oil |
| 12 | Br | " | " | " | " |
| 13 | " | Br | " | " | 67 |
| 14 | Cl | H | " | " | Oil |
| 15 | " | Br | Br | " | " |
| 16 | Br | Br | Br | " | Oil |
| 17 | Cl | Cl | Cl | " | " |
| 18 | H | H | H | C$_3$H$_7$—CH=CH—CH$_2$— | " |
| 19 | " | " | " | C$_2$H$_5$—C≡C—CH$_2$— | " |
| 20 | " | " | " | C$_3$H$_7$—C≡C—CH$_2$— | " |
| 21 | " | " | " | CH$_3$—(CH$_2$)$_{10}$—CH$_2$ | Oil |
| 22 | Cl | " | " | " | " |
| 23 | H | " | " | cyclohexyl | " |
| 24 | " | " | " | CH$_3$OOC—CH$_2$— | Oil |
| 25 | Cl | " | " | " | " |
| 26 | Br | " | " | " | " |
| 27 | " | Br | " | " | 101 |
| 28 | " | " | Br | " | 72 |
| 29 | H | H | H | CH$_3$OOC—(CH$_2$)$_2$— | Oil |
| 30 | " | " | " | CH$_3$OOC—(CH$_2$)$_3$— | Oil |
| 31 | Cl | " | " | " | Oil |
| 32 | H | " | " | CH$_3$OOC—(CH$_2$)$_4$— | Oil |
| 33 | " | " | " | CH$_3$OOC—CH(CH$_3$)— | Oil |
| 34 | " | " | " | ICH$_2$—(CH$_2$)$_2$— | Oil |
| 35 | " | " | " | C$_6$H$_5$—CH$_2$— | bp.$_{0.5}$146 |
| 36 | " | " | " | Cl—C$_6$H$_4$—CH$_2$— | 44 |
| 37 | " | " | " | (CH$_3$)$_3$C—CO—CH$_2$— | 33 |
| 38 | Cl | " | " | " | 68 |
| 39 | H | " | " | Cl—C$_6$H$_4$—CO—CH$_2$— | 124 |
| 40 | " | " | " | O$_2$N,Cl—C$_6$H$_3$— | 69 |
| 41 | Cl | " | " | O$_2$N,Cl—C$_6$H$_3$— | Oil |
| 42 | " | Br | Br | " | " |

TABLE 1-continued

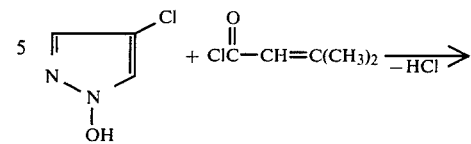

n = 0

| Example | R¹ | R² | R³ | R⁴ | Mp. [°C.] |
|---|---|---|---|---|---|
| 43 | H | H | H | O₂N—⬡—NO₂ (CH₃) | 116 |
| 44 | Cl | " | " | " | Oil |
| 45 | Br | " | " | " | " |
| 46 | H | " | " | CF₃—⬡—NO₂ | 66 |
| 47 | I | " | " | " | 63 |
| 48 | Br | " | " | " | Oil |
| 49 | Cl | " | " | " | " |
| 50 | " | Br | Br | " | " |
| 51 | H | H | H | CH₃—CO—⬡—NO₂ | " |

EXAMPLE 53

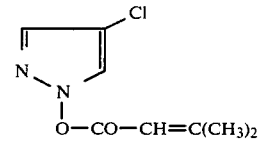

20 g of dimethylacrylyl chloride, dissolved in 100 g of acetonitrile, are added to 20 g of 4-chloro-1-hydroxypyrazole, 20 g of sodium carbonate and 150 g of acetonitrile at 25° C., while stirring. Stirring is continued for 12 hours at 25° C., after which the solid product is filtered off under suction and washed with 100 g of acetonitrile. The solution is evaporated down at 40° C. and under 20 mbar, the residue is taked up in 200 g of dichloromethane, the solution is extracted 3 times with 200 g of saturated aqueous sodium bicarbonate solution, the organic phase is dried with magnesium sulfate and evaporated down, and the residue is digested with 300 g of petroleum ether. 30.5 g (90% of theory) of 4-chloropyrazol-1-yl 3,3-dimethylacrylate of melting point 71° C. are obtained.

TABLE 2

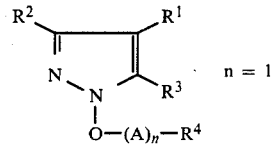

n = 1

| Example | R¹ | R² | R³ | A | R⁴ | Mp. [°C.] |
|---|---|---|---|---|---|---|
| 53 | H | H | H | CO | CH₃— | bp.₂₀ 95 |
| 54 | " | " | " | SO₂ | " | 34 |
| 55 | Cl | " | " | CO₂ | " | Oil |
| 56 | Br | " | " | CO | " | " |
| 57 | " | Br | " | CO₂ | " | " |
| 58 | " | " | Br | " | " | 65 |
| 59 | Cl | " | " | CO | " | 87 |
| 60 | " | " | " | " | C₂H₅— | 83 |
| 61 | " | " | " | " | C₃H₇— | 41 |
| 62 | H | H | H | SO₂ | (CH₃)₂CH— | Oil |
| 63 | " | " | " | SO₂NH | " | 79 |
| 64 | Cl | " | " | " | " | 104 |
| 65 | Br | Br | " | " | " | 142 |
| 66 | H | H | " | CO₂ | " | Oil |
| 67 | Cl | " | " | " | " | " |
| 68 | Br | " | " | " | " | " |
| 69 | " | Br | " | " | " | " |
| 70 | " | " | Br | " | " | " |
| 71 | H | H | H | CO |  | 35 |
| 72 | " | " | " | " | 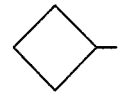 | Oil |

TABLE 2-continued

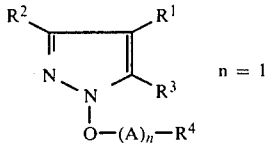

n = 1

| Example | R¹ | R² | R³ | A | R⁴ | Mp. [°C.] |
|---|---|---|---|---|---|---|
| 73 | " | " | " | " |  | " |
| 74 | " | " | " | " | 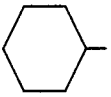 | " |
| 75 | " | " | " | CO₂ | " | " |
| 76 | " | " | " | CO | $(CH_3)_3C-$ | " |
| 77 | Cl | " | " | " | " | " |
| 78 | H | " | " | " | $(CH_3)_2CH-CH_2-$ | " |
| 79 | Cl | " | " | " | " | " |
| 80 | H | " | " | " | $(CH_3)_3C-CH_2-$ | " |
| 81 | Cl | " | " | " | " | " |
| 82 | H | " | " | " | $CH_2=C(CH_3)-$ | " |
| 83 | Cl | " | " | " | " | " |
| 84 | H | " | " | " | $CH_3-CH=C(CH_3)-$ | " |
| 85 | Cl | " | " | " | " | " |
| 86 | H | " | " | " | $HC\equiv C-CH_2-$ | bp.₁50 |
| 87 | " | " | " | " | $CH_3-(CH_2)_7-$ | 30 |
| 88 | " | " | " | " | $CH_3-CH=CH-$ | 58 |
| 89 | Cl | " | " | " | " | 34 |
| 90 | Br | " | " | " | " | 60 |
| 91 | " | Br | " | " | " | 86 |
| 92 | " | H | " | " | $(CH_3)_2C=CH-$ | 69 |
| 93 | H | " | " | " | " | 44 |
| 94 | Br | Br | " | " | " | 57 |
| 95 | " | " | Br | " | " | 61 |
| 96 | " | " | " | CO | $CH_3-CH=CH-$ | 94 |
| 97 | Cl | " | " | " | $CH_3-(CH_2)_7-$ | Oil |
| 98 | " | " | " | " | $CH_3-(CH_2)_{16}-$ | 94 |
| 99 | " | " | " | " | $CH_3-(CH_2)_7-CH=CH-(CH_2)_7-$ | Oil |
| 100 | " | H | H | " | $CH_2=CH-(CH_2)_8-$ | " |
| 101 | H | " | " | " | " | " |
| 102 | " | " | " | SO₂ | $C_6H_5-CH=CH-$ | " |
| 103 | " | " | " | CO | " | 86 |
| 104 | Cl | " | " | SO₂ | " | Oil |
| 105 | " | " | " | CO | " | 80 |
| 106 | H | " | " | CO₂ | 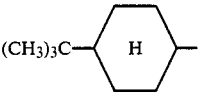 | 55 |
| 107 | " | " | " | CO | $C_6H_5-CH(Cl)-$ | 39 |
| 108 | " | " | " | " | $2,4-DiCl-C_6H_3-O-CH_2-$ | 85 |
| 109 | " | " | " | CO₂ | $ClCH_2-CH_2-$ | Oil |
| 110 | " | " | " | " | $CH_3O-CH_2-CH_2-$ | " |
| 111 | " | " | " | CO | $CH_3-CH(Cl)-$ | " |
| 112 | " | " | " | " | $Cl-CH_2-CH_2-$ | " |
| 113 | " | " | " | " | $CH_3-CH(Br)-$ | 54 |
| 114 | " | " | " | CO₂ | $ClH_2-CH_2-CH_2-$ | Oil |
| 115 | Cl | " | " | SO₂ | $C_6H_5$ | " |
| 116 | Br | " | " | " | " | 50 |
| 117 | H | " | " | " | 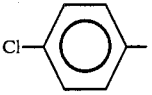 | 73 |
| 118 | Cl | " | " | " | " | Oil |
| 119 | H | " | " | CO | " | 75 |
| 120 | " | " | " | CO₂ | $C_6H_5-$ | 65 |
| 121 | Cl | Br | Br | CO | " | 86 |

TABLE 2-continued $$\underset{\underset{O-(A)_n-R^4}{|}}{\overset{R^2}{\underset{N}{\bigvee}}}\overset{R^1}{\underset{R^3}{\bigvee}} \quad n = 1$$

| Example | R¹ | R² | R³ | A | R⁴ | Mp. [°C.] |
|---|---|---|---|---|---|---|
| 122 | Br | H | H | SO₂ | Cl—C₆H₄— (4-Cl-phenyl) | 92 |
| 123 | Cl | Br | Br | CO | " | 105 |
| 124 | H | H | H | SO₂ | 2,4,5-TriCl—C₆H₂— | 85 |
| 125 | Cl | " | " | " | " | 92 |
| 126 | Br | " | " | " | " | 103 |
| 127 | " | Br | " | " | " | 106 |
| 128 | " | " | " | " | 4-Cl—C₆H₄— | Oil |
| 129 | I | H | " | " | C₆H₅— | 62 |
| 130 | " | " | " | " | 4-Cl—C₆H₄— | 100 |
| 131 | Br | Br | Br | " | " | 142 |
| 132 | H | H | H | SO₂ | 4-CH₃—C₆H₄— | 45 |
| 133 | " | " | " | " | O₂N—C₆H₃(CCl₃)— | 148 |
| 134 | Cl | " | " | " | " | 87 |

EXAMPLE 135

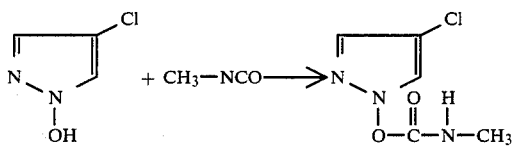

8 g of methyl isocyanate, dissolved in 50 g of acetonitrile, are added to 15 g of 4-chloro-1-hydroxypyrazole and 150 g of acetonitrile at 25° C., while stirring. Stirring is continued for 12 hours, after which the reaction mixture is evaporated down and the residue is digested 3 times with a total of 150 g of petroleum ether. 17.8 g (80% of theory) or 4-chloropyrazol-1-yl N-methylcarbamate of melting point 125° C. are obtained.

TABLE 3

$$\underset{\underset{O-(A)_n-R^4}{|}}{\overset{R^2}{\underset{N}{\bigvee}}}\overset{R^1}{\underset{R^3}{\bigvee}} \quad A = -\overset{O}{\underset{\|}{C}}-\overset{H}{\underset{|}{N}}-\\ n = 1$$

| Example | R¹ | R² | R³ | R⁴ | Mp. [°C.] |
|---|---|---|---|---|---|
| 136 | H | H | H | CH₃— | 96 |
| 137 | I | H | H | CH₃— | 158 |
| 138 | Br | Br | H | CH₃— | 148 |
| 139 | Br | Br | Br | CH₃— | 156 |
| 140 | H | H | H | C₄H₉— | 59 |

TABLE 3-continued $$\underset{\underset{O-(A)_n-R^4}{|}}{\overset{R^2}{\underset{N}{\bigvee}}}\overset{R^1}{\underset{R^3}{\bigvee}} \quad A = -\overset{O}{\underset{\|}{C}}-\overset{H}{\underset{|}{N}}-\\ n = 1$$

| Example | R¹ | R² | R³ | R⁴ | Mp. [°C.] |
|---|---|---|---|---|---|
| 141 | H | H | H | cyclohexyl | 117 |
| 142 | H | H | H | 3,4-Cl₂-C₆H₃— | 178 |
| 143 | Br | H | H | " | 225 |
| 144 | Br | Br | Br | " | 174 |

EXAMPLE 145

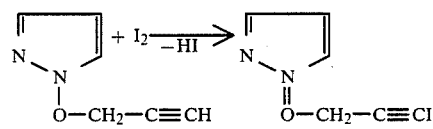

41.6 g of iodine are added, a little at a time, to 20 g of 1-pyrazolyl propargyl ether and 20 g of sodium carbonate in 400 g of acetonitrile at 40° C., while stirring.

Stirring is continued for 8 hours at 40° C., after which undissolved material is filtered off under suction, and the filtrate is evaporated down in a rotary evaporator at 30° C. and under 20 mbar. The residue is dissolved in 200 g of dichloromethane, the solution is extracted twice with 200 g of 10% strength aqueous sodium thiosulfate solution, and the organic phase is dried with magnesium sulfate and evaporated down. 40 g (99% of theory) of 1-pyrazolyl iodopropargyl ether are obtained as an oil (H$^1$—NMR, in ppm: 5.1, s, 2H; 6.2, m, 1H; 7.4, m, 2H).

TABLE 4

$$\begin{array}{c} R^2 \diagdown \diagup R^1 \\ \| \\ N \diagdown \diagup R^3 \\ N \\ | \\ O_5-(A)_n-CH_2-C\equiv Cl \end{array} \quad \begin{array}{l} n = 0 \\ R^4 = -CH_2-C\equiv Cl \end{array}$$

| Example | R$^1$ | R$^2$ | R$^3$ | Mp. [°C.] |
|---|---|---|---|---|
| 146 | Cl | H | H | Oil |
| 147 | Br | H | H | Oil |
| 148 | Br | Br | H | Oil |
| 149 | Br | Br | Br | Oil |
| 150 | Cl | Br | Br | Oil |
| 151 | I | H | H | Oil |
| 152 | Cl | Cl | Cl | Oil |

EXAMPLE 159

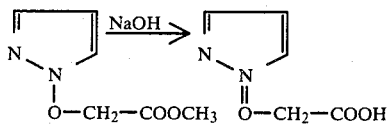

15.6 g of methyl pyrazol-1-yloxy acetate and 8 g of 50% strength aqueous sodium hydroxide solution are stirred for 3 hours at 50° C. The mixture is acidified to pH 2 with 10% strength hydrochloric acid, and extracted twice with 200 g of dichloromethane. The organic phase is dried with magnesium sulfate and evaporated down. 10.5 g (75% of theory) of pyrazol-1-yloxyacetic acid of melting point 99° C. are obtained.

TABLE 5

$$\begin{array}{c} R^2 \diagdown \diagup R^1 \\ \| \\ N \diagdown \diagup R^3 \\ N \\ | \\ O-(A)_n-R^4 \end{array} \quad n = 0$$

| Example | R$^1$ | R$^2$ | R$^3$ | R$^4$ | [°C.] |
|---|---|---|---|---|---|
| 154 | Cl | H | H | HOOC—CH$_2$— | 104 |
| 155 | Br | H | H | " | 66 |
| 156 | Br | Br | Br | " | 84 |
| 157 | H | H | H | HOOC—(CH$_2$)$_2$— | 51 |
| 158 | H | H | H | HOOC—(CH$_2$)$_3$— | 48 |
| 159 | Cl | H | H | " | 73 |
| 160 | H | H | H | HOOC—(CH$_2$)$_4$— | 32 |
| 161 | H | H | H | HOOC—CH(CH$_3$)— | 124 |

| Example | δ[ppm] |
|---|---|
| 11 | 2.65,t, 1H; 4.9,d, 2H; 7.3,s, 1H; 7.7,s, 1H |
| 12 | 2.7,t, 1H; 4.9,d, 2H; 7.3,s, 1H; 7.5,s, 1H |
| 14 | 2.65,t, 1H; 4.9,d, 2H; 7.25,s, 1H; 7.5,s, 1H |
| 15 | 2.7,t, 1H; 4.9,d, 2H |
| 16 | 2.65,t, 1H; 4.9,d, 2H |
| 17 | 2.65,t, 1H; 4.9,d, 2H |
| 18 | 0.7–2.2,m, 7H; 4.7,m, 2H; 5.7,m, 1H; 6.1,m, 1H; 7.3,d, 2H |
| 19 | 1.1,t, 3H; 2.2,m, 2H; 4.9,m, 2H; 6.2,m, 1H; 7.4,m, 2H |
| 20 | 0.9,t, 3H; 1.4,m, 2H; 2.2,m, 2H; 4.9,s, 2H; 6.2,m, 1H; 7.4,m, 2H |
| 21 | 0.9,m, 3H; 1.3,m, 20H; 4.3,m, 2H; 6.2,t, 1H; 7.3,m, 2H |
| 22 | 0.9,m, 3H; 1.3,m, 20H; 4.3,m, 2H; 7.2,s, 1H; 7.5,s, 1H |
| 24 | 3.8,s, 3H; 4.9,s, 2H; 6.2,t, 1H; 7.2,m, 1H; 7.5,m, 1H |
| 25 | 3.8,s, 3H; 4.9,s, 2H; 7.25,s, 1H; 7.5,s, 1H |
| 26 | 3.7,s, 3H; 4.8,s, 2H; 7.2,s, 1H;7.6,s, 1H |
| 29 | 1.2,t, 3H; 2.7,t, 2H; 4.3,m, 4H; 6.2,m, 1H; 7.3,m, 2H |
| 30 | 2.4,m, 4H; 3.7,s, 3H; 4.3,m, 2H; 6.1,t, 1H; 7.3,m, 2H |
| 31 | 2.4,m, 4H; 3.7,s, 3H; 4.3,m, 2H; 7.2,s, 1H; 7.5,s, 1H |
| 32 | 2.0,m, 4H; 2.5,m, 2H; 3.7,s, 3H; 4.3,m, 2H; 6.2,m, 1H; 7.3,m, 2H |
| 33 | 1.5,d, 3H; 3.6,s, 3H; 5.0,mm 1H; 6.0,t, 1H; 7.25,m, 2H |
| 34 | 2.1,m, 2H; 3.3,t, 2H; 4.4,t, 2H; 6.1,t, 1H; 7.2,m, 2H |
| 41 | 6.6,d, 1H; 7.5,d, 2H; 8.1,m, 1H; 8.4,d, 1H |
| 42 | 6.6,d, 1H; 8.1,m, 1H; 8.4,d, 1H |
| 44 | 6.9,d, 1H; 7.6,d, 2H; 8.4,m, 1H; 8.9,d, 1H |
| 45 | 6.8,d, 1H; 7.5,d, 2H; 8.3,m, 1H; 8.8,d, 1H |
| 48 | 6.8,d, 1H; 7.35,s, 1H; 7.6–8.3,m, 3H |
| 50 | 6.6,d, 1H; 7.6,m, 1H; 8.1,d, 1H |
| 51 | 2.6,s, 3H; 6.4,m, 2H; 7.4,d, 1H; 7.6,d, 1H; 8.0,m, 1H; 8.5,d, 1H |
| 55 | 4.1,s, 3H; 7.4,d, 2H |
| 56 | 4.0,s, 3H; 7.35,d, 2H |
| 57 | 4.0,s, 3H; 7.4,s, 1H |
| 62 | 2.6,d, 6H; 3.9,m, 1H; 6.3,t, 1H; 7.4,m, 2H |
| 66 | 1.4,d, 6H; 5.05,m, 1H; 6.3,t, 1H; 7.4,m, 2H |
| 67 | 1.4,d, 6H; 5.1,m, 1H; 7.4,m, 2H |
| 68 | 1.4,d, 6H; 5.0,m, 1H; 7.4,d, 2H |
| 69 | 1.4,d, 6H; 5.05,m, 1H; 7.4,s, 1H |
| 70 | 1.4,d, 6H; 5.1,m, 1H |
| 72 | 2.2,m, 6H; 3.3,m, 1H; 6.3,t, 1H; 7.3,m, 2H |
| 73 | 1.3–2.3,m, 8H; 2.0,m, 1H; 6.3,m, 1H; 7.3,m, 2H |
| 74 | 1.2–3.0,m, 11H; 6.4,t, 1H; 7.4,m, 2H |
| 75 | 1.5,m, 10H; 4.7,m, 1H; 6.2,m, 1H; 7.3,m, 2H |
| 76 | 1.4,s, 9H; 6.35,t, 1H; 7.4,m, 2H |
| 77 | 1.4,s, 9H; 7.4,m, 2H |
| 78 | 1.0,d, 6H; 2.3,m, 3H; 6.3,t, 1H; 7.4,m, 2H |
| 79 | 1.1,d, 6H; 2.4,m, 3H; 7.4,d, 2H |
| 80 | 1.2,s, 9H; 2.5,s, 2H; 6.4,t, 1H; 7.4,m, 2H |
| 81 | 1.2,s, 9H; 2.5,s, 2H; 7.3,m, 2H |
| 82 | 2.1,d, 3H; 5.9,bs, 1H; 6.4,m, 2H; 7.4,d, 2H |
| 83 | 2.1,d, 3H; 5.9,bs, 1H; 6.5,bs, 1H |
| 84 | 1.9,d, 6H; 6.4,t, 1H; 7.3,m, 3H |
| 85 | 1.9,d, 6H; 7.4,m, 3H |
| 97 | 0.7–1.9,m, 15H; 2.5,m, 2H |
| 99 | 0.7–2.7,m, 31H; 5.3,m, 2H |
| 100 | 1.1–2.8,m, 16H; 4.8–5.3,m, 2H; 5.5–6.2,m, 1H; 7.4,m, 2H |
| 101 | 1.1–2.8,m, 16H; 4.8–5.3,m, 2H; 5.5–6.4,m, 2H; 7.4,m, 2H |
| 102 | 6.3,m, 1H; 6.65–7.7,m, 9H |
| 104 | 6.7–7.7,m, 9H |
| 109 | 3.7,t, 2H; 4.5,t, 2H; 6.2,t, 1H; 7.4,m, 2H |
| 110 | 3.4,s, 3H; 3.6,m, 2H; 4.5,m, 2H; 6.3,t, 1H; 7.4,m, 2H |
| 111 | 1.7,t, 1H; 4.5,m, 1H; 6.15,m, 1H; 7.3,m, 2H |
| 112 | 3.0,t, 2H; 3.8,t, 2H; 6.3,t, 1H; 7.3,d, 2H |
| 114 | 2.25,m, 2H; 2.8,t, 2H; 3.60,t, 2H; 6.3,t, 1H; 7.3,d, 2H |
| 115 | 7.2,s, 1H; 7.4–8.1,m, 6H |
| 118 | 7.1,s, 1H; 7.3–8.1,m, 5H |
| 128 | 7.5–8.0,m, 5H |
| 146 | 5.2,s, 2H; 7.4,m, 2H |
| 147 | 5.1,s, 2H; 7.35,m, 2H |
| 148 | 5.2,s, 2H; 7.3,m, 2H |
| 149 | 5.2,s, 2H |
| 150 | 5.15,s, 2H |
| 151 | 5.2,s, 2H |
| 152 | 5.2,s, 2H; 7.25,s, 1H; 7.6,s, 1H |

USE EXAMPLE 220 mg of ammonium sulfate were added to 200 g of an unsterilized loamy sand which was taken from open ground and whose moisture content had been brought to 50% of the maximum water capacity. The ammonium sulfate was mixed thoroughly with the soil, after which the active ingredients, dissolved in 0.2 ml of acetone, were added in amounts of, in each case, 1 ppm, based on moist sand soil. The soil samples were carefully stirred up, the acetone was allowed to evaporate and the soil samples were incubated, together with the controls without added active ingredient, at 21° C. for 28 days, in 1 liter beakers covered with aluminum foil to prevent loss of water. (After this period, a soil sample with normal soil conditions generally no longer contains any detectable amounts of ammonium nitrogen).

Thereafter, 2.5 of each of the soil samples were introduced into 100 ml conical flasks and 22.5 ml of 0.1 N potassium sulfate solution were added. After it had been shaken for 30 minutes, the mixture was filtered and 2.5 ml of each of the soil extracts were mixed with 1625 ml of distilled water. To detect any ammonium ions still present in the soil extract, 1.25 ml of Nessler reagent were then added, and the mixture thoroughly shaken. The color changes were then measured photometrically at a wavelength of 420 nm. The amounts of ammonium sulfate still present in the soil samples were determined with reference to standard curves determined by measurement of solutions containing known amounts of ammonium sulfate. The percentage inhibition of nitrification in the treated soil samples was calculated by comparison with the untreated soil sample (only ammonium sulfate added), using the following formula:

$$\ldots \% \text{ inhibition of nitrification} = a - b \cdot 100$$

a = rate of nitrification for ammonium sulfate (assumed to be 100% or 1.0)

b = rate of nitrification for ammonium sulfate + nitrification inhibitor

| Active ingredient of Example | ... % inhibition of nitrification 4 weeks after the addition of 1 ppm of active ingredient to the soil |
| --- | --- |
| 1 | 100 |
| 2 | 87 |
| 14 | 100 |
| 25 | 92 |
| 38 | 100 |
| 47 | 83 |
| 48 | 84 |
| 52 | 90 |
| 55 | 88 |
| 56 | 93 |
| 64 | 100 |
| 65 | 94 |
| 67 | 88 |
| 68 | 89 |
| 69 | 73 |
| 89 | 85 |
| 90 | 95 |
| 91 | 92 |

-continued

| Active ingredient of Example | ... % inhibition of nitrification 4 weeks after the addition of 1 ppm of active ingredient to the soil |
| --- | --- |
| 94 | 86 |
| 100 | 90 |
| 105 | 95 |
| 115 | 100 |
| 116 | 86 |
| 118 | 100 |
| 122 | 79 |
| 124 | 88 |
| 125 | 86 |
| 126 | 86 |
| 134 | 96 |
| 135 | 100 |
| 137 | 73 |
| 138 | 88 |
| 145 | 100 |
| 146 | 100 |
| 154 | 100 |
| 163 | 100 |
| Comparison 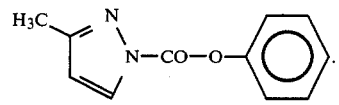 | 69 |

(Active ingredient No. 95 from German Laid-Open Application DOS No. 2,745,833).

We claim:

1. A composition of matter which is a 1-hydroxypyrazole derivative of the formula (I)

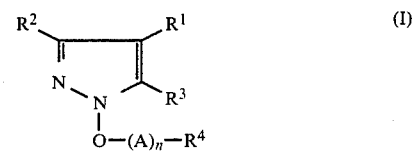

where A is

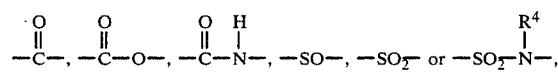

n is 0 or 1, $R^1$, $R^2$ and $R^3$ independently of one another are each hydrogen, chlorine, bromine or iodine, and $R^4$ is hydrogen, a straight-chain or branched, open-chain alkyl, alkenyl or alkynyl radical, a cyclic alkyl, alkenyl or alkynyl radical or carbocyclic aryl or carbocyclic aralkyl, with the proviso that $R^4$ is not hydrogen when n is 0, and the radicals $R^4$ which are capable of being substituted may furthermore be monosubstituted or polysubstituted by halogen, haloalkyl, haloalkoxy, alkyl, alkoxy, alkoxycarbonyl, —OH, =O, —COOH or a salt of this, —$NO_2$ or —CN.

2. A method of inhibiting nitrification of ammonium nitrogen in the soil which comprises treating the soil with an effective amount of a nitrification-inhibiting composition as defined by claim 1.

* * * * *